United States Patent [19]

Kendall

[11] Patent Number: 5,956,383
[45] Date of Patent: Sep. 21, 1999

[54] APPARATUS FOR REMOVING HEAT FROM X-RAY TUBE COOLING FLUID

[75] Inventor: Charles B. Kendall, Brookfield, Wis.

[73] Assignee: General Electric Company, Milwaukee, Wis.

[21] Appl. No.: 08/745,163

[22] Filed: Nov. 7, 1996

[51] Int. Cl.[6] .................................................. H01J 35/10
[52] U.S. Cl. ........................ 378/199; 378/200; 378/141
[58] Field of Search ................................... 378/199–201, 378/130, 141, 4

[56] References Cited

U.S. PATENT DOCUMENTS

| | | | |
|---|---|---|---|
| 4,866,743 | 9/1989 | Kroener | 378/199 |
| 4,969,167 | 11/1990 | Zupancic et al. | 378/199 |

Primary Examiner—Don Wong
Attorney, Agent, or Firm—James O. Skarsten; John H. Pilarski

[57] ABSTRACT

In an arrangement for cooling an X-ray tube mounted on the gantry of a CT system, a path of flow is established by means of conduits or the like for circulating a cooling fluid between the tube and a heat exchanger. As fluid passes through the heat exchanger, a stream of air is applied to the path of flow, by means of a radial fan, to carry heat away from the fluid. The axis of the fan is maintained in parallel relationship with the axis of the gantry, to prevent gyroscopic loading of the fan as the fan rotates about the gantry axis with the gantry. The fan comprises a device for exhausting air heated by the exchange process radially, with respect to the fan axis, to minimize fan-generated acoustic noise while maintaining good thermal performance. Fan support structure lying in the path of the exhausted air is selectively shaped to reduce air flow turbulence, and to thereby further reduce fan noise.

12 Claims, 3 Drawing Sheets

APPARATUS FOR REMOVING HEAT FROM X-RAY TUBE COOLING FLUID

BACKGROUND OF THE INVENTION

The invention disclosed and claimed herein is generally directed to apparatus for cooling the oil or other fluid which is used to carry heat away from the X-ray tube in a computed tomography (CT) diagnostic imaging system. More particularly, the invention is directed to apparatus of such type which significantly reduces acoustic noise which is likely to disturb or annoy CT imaging patients and operating personnel.

As is well known in the art, an X-ray tube generates substantial amounts of heat in the course of its operation. Accordingly, provision must be made for removing heat from the proximity of the tube, and for dispersing the heat into the surrounding environment. In a common arrangement, a coolant fluid or oil, such as a product sold by Exxon under the name UNI-Volt, circulates around the tube to receive excessive heat, and then flows through a first hose, conduit, or the like to a heat exchanger. The exchanger causes the heat stored in the oil to be exposed to the surrounding air, so that the heat can be convected thereinto. The cooled oil then flows back to the tube through a second hose or conduit.

Cooling arrangements of the above type commonly employ a fan to move air past or through the heat exchanger, to enhance heat transfer. If the X-ray tube is used in connection with a CT system, the tube, the heat exchanger, and the cooling fan are respectively mounted on an annular gantry, which is rapidly rotated around the patient to acquire a CT image. The gantry may rotate, for example, at 90 rpm. At present, the X-ray tube cooling fans used in CT systems tend to be axial. That is, both the intake and exhaust air streams generated by the fan are directed along the fan axis, i.e., the axis of blade rotation. Herein, "intake" and "exhaust" air streams mean the streams or quantities of air which are respectively moved into and out of a fan by operation thereof. To provide sufficient cooling power, axial cooling fans must be rotated at a speed on the order of 3600 rpm.

In order to resist vibration and provide some measure of sturdiness or rigidity, axial fans generally have a number of struts or like members positioned around the outer edges of the fan blades, in spaced apart relationship. Each time a blade passes by one of the struts, an acoustic noise is produced. For the fan rotational speed stated above, the pure tone, or first harmonic of such noise will exceed 500 Hz. Accordingly, the second and higher harmonics of such noise will exceed 1000 Hz. As is known by those of skill in the art, 1000 Hz is a very significant threshold in reducing the "annoyance factor" associated with acoustic noise. That is, acoustic noise having principal frequency components which exceed 1000 Hz tends to be much more disturbing than noise which does not include such components.

The 1000 Hz threshold and the associated acoustic noise "annoyance factor" are of particular significance in regard to X-ray tube cooling systems for use in CT applications. When a CT system is being operated to acquire an image, the patient or other imaging subject must remain as still as possible, for a period of time. Accordingly, it is desirable to minimize bothersome noises as much as possible, to avoid distracting, irritating, or in some cases, frightening, the patient. Excessive noise may also be disturbing to persons operating the CT system. Higher frequency gantry sound can also interfere with the patient speaker and microphone used in most systems to maintain continuous patient communication.

One approach to relieving noise generated by a prior art cooling fan would be to reduce the rotational speed thereof. Principal frequency components of acoustic noise generated by the fan could thereby be reduced below the 1000 Hz threshold. However, the air flow provided by the fan to the heat exchanger would also be significantly reduced thereby, so that the thermal performance of the X-ray tube cooling system could be significantly diminished.

SUMMARY OF THE INVENTION

Apparatus is provided for removing heat from fluid used to cool an X-ray tube mounted on the gantry of a CT system, the gantry rotating about a gantry axis. The apparatus comprises a frame fixably joined to the gantry for rotation therewith, and further comprises means for providing a path of flow for the cooling fluid between the X-ray tube and a location proximate to the frame, a portion of the path lying within a specified spatial volume. A radial fan is provided for moving a stream of air through the spatial volume to remove heat from the cooling fluid as it flows through the portion of the path. The radial fan comprises an arrangement of blades or impellers, which rotate about a fan axis to draw the stream of air through the spatial volume into the impeller blade arrangement, and thereafter radially exhaust the air. Means are provided for mounting the radial fan on the frame so that the fan axis of rotation is in substantially parallel relationship with the gantry axis.

In a preferred embodiment, the frame includes a selected number of flat structural members positioned in spaced-apart relationship from the fan impellers. Each of the flat members lies in the path of the radially exhausted air, and has side edges which are selectively shaped to reduce turbulence in the exhausted air flow, and to thereby reduce noise caused by such turbulence. Preferably, the side edges of each of the flat structural members is provided with a selected bend radius.

OBJECTS OF THE INVENTION

An object of the invention is to significantly reduce noise in a system disposed to remove heat from X-ray tube cooling oil or fluid.

Another object is to provide a system of the above type which significantly reduces noise while maintaining good thermal performance.

Another object is to provide a system of the above type which employs a radial fan as an integral component.

Another object is to provide a system of the above type for use in a computed tomography imaging system, wherein gyroscopic loading of the fan is substantially eliminated, to prolong the life of the fan.

These and other objects of the invention will become more readily apparent from the ensuing specification, taken together with the accompanying drawings.

DESTAILED DESCRIPTION OF THE PREFERRED EMBODIMENT

Figure 1:
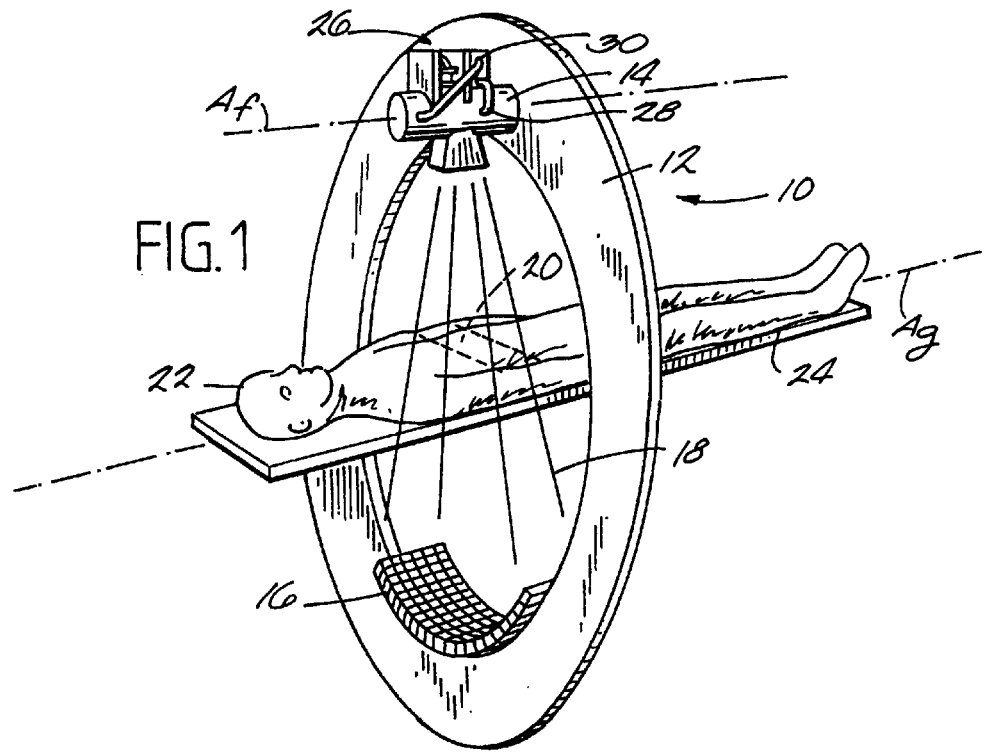
FIG. 1 is a perspective view showing selected components of a CT imaging system, together with an embodiment of the invention.

Referring to FIG. 1, there are shown certain components of a CT system 10, including an annular shaped gantry 12 disposed for rotation about a gantry axis $A_g$. An X-ray tube 14 and an array 16 of X-ray detector elements are both supportably mounted on gantry 12, for rotation therewith, on opposing sides of the gantry. X-ray tube 14 projects an X-ray beam 18 toward the array 16, the beam passing through a section 20 of a patient 22 carried upon a couch or other patient support platform 24. As gantry 12 rotates about its axis, X-ray data representing body structure of patient 22 lying within the section 20 is acquired by element array 16. The acquired data may be employed to construct an image of such body structure, following techniques and practices which are very well known to those of skill in the computed tomography arts. It will be understood that certain other CT system components, such as a data processing and image reconstruction system, as well as means for supporting and rotatably driving the gantry 12, are conventional and likewise well known to those of skill in the CT arts. Accordingly, such components are not shown in FIG. 1. CT systems are described in further detail, for example, in US Pat. Nos. 5,473,654 and 5,473,655, both issued Dec. 5, 1995. Teachings thereof are incorporated herein by reference.

As stated above, X-ray tube 14 may generate substantial amounts of excess heat in the course of CT imaging. Accordingly, a cooling arrangement 26, incorporating an embodiment of the invention and described hereinafter in further detail, is also mounted to gantry 12 for rotation therewith. To remove the excess heat from the tube 14, a cooling oil or fluid, such as the UNI-VOLT product of Exxon referred to above (not shown in FIG. 1) is circulated around X-ray tube 14, so that heat is transferred to the cooling oil from the tube. The heated oil flows through a hose or conduit 28 to cooling arrangement 26, which removes heat from the oil and transfers it to the air. The cooled oil then flows back to X-ray tube 14 through a hose or conduit 30.

Referring further to FIG. 1, there is shown cooling arrangement 26 having an axis $A_f$, which, as described hereinafter, is the axis of a cooling fan incorporated therein. Cooling arrangement 26 is fixably mounted to gantry 12 either directly or by attachment to tube 14, so that axis $A_f$ remains in parallel relationship with the gantry axis $A_g$ as the gantry 12 rotates. Significant advantages in establishing and maintaining such parallel relationship between axes $A_g$ and $A_f$ are likewise described hereinafter.

Figure 2:
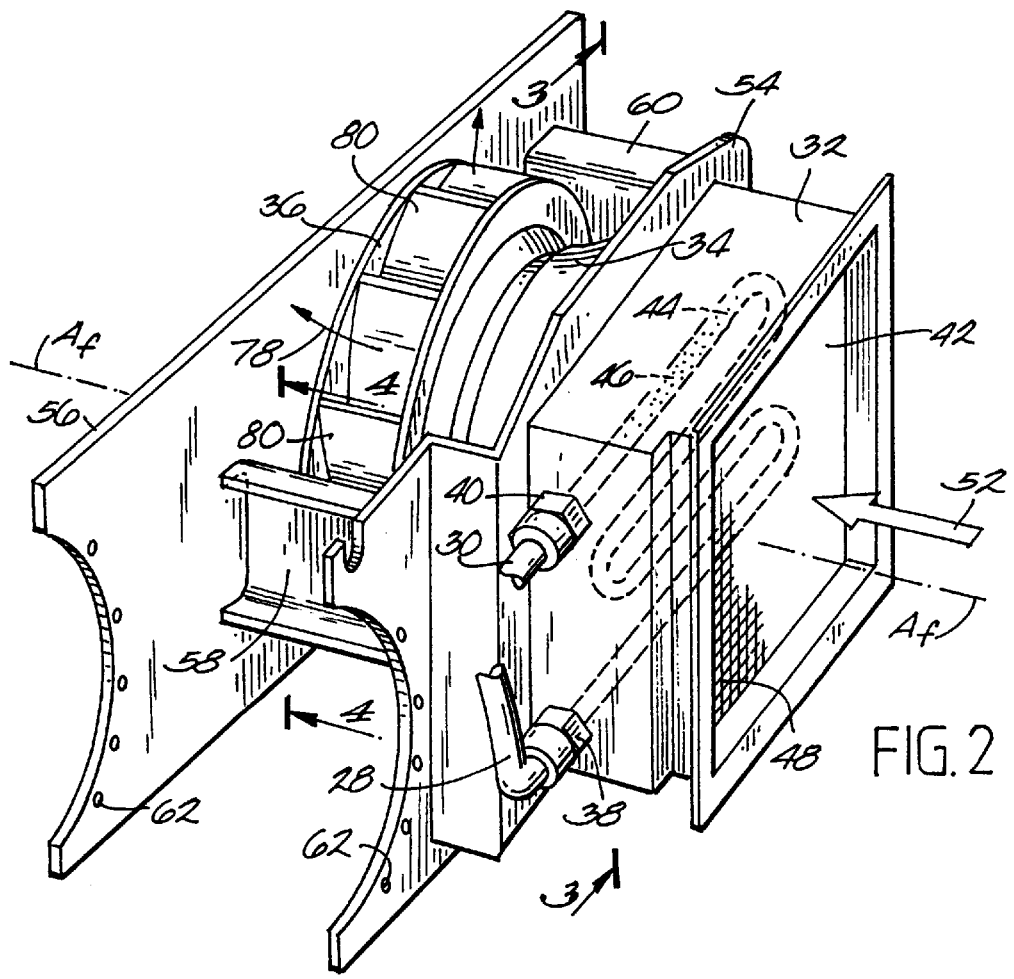
FIG. 2 is a perspective view showing the embodiment of FIG. 1 in greater detail.

Referring to FIG. 2, there is shown cooling arrangement 26 generally comprising a heat exchanger 32, an air shroud 34, and a fan 36, which comprises a radial fan. Heat exchanger 32 is provided with an inlet port 38 connected to hose 28, an outlet port 40 connected to hose 30, and an interior chamber 42. Chamber 42 contains tubing 44, which has its two ends respectively coupled to outlet ports 38 and 40. Thus, tubing 44 together with hoses 28 and 30 provides a closed path for the flow of cooling oil 46 from X-ray tube 14 through heat exchanger 32 and then back to tube 14. FIG. 2 shows tubing 44 shaped to have multiple U-shaped bends, in order to maximize the length of the path of cooling oil flow which lies in chamber 42. FIG. 2 further shows a dust screen 48 placed over the right side of heat exchanger 32, as viewed in FIG. 2. It is to be understood that various designs for heat exchanger 32 are well known to those of skill in the X-ray tube cooling arts. Particular details of the heat exchanger shown herein are primarily intended to illustrate the operation of a conventional X-ray tube heat exchanger, rather than a specific device.

Figure 3:
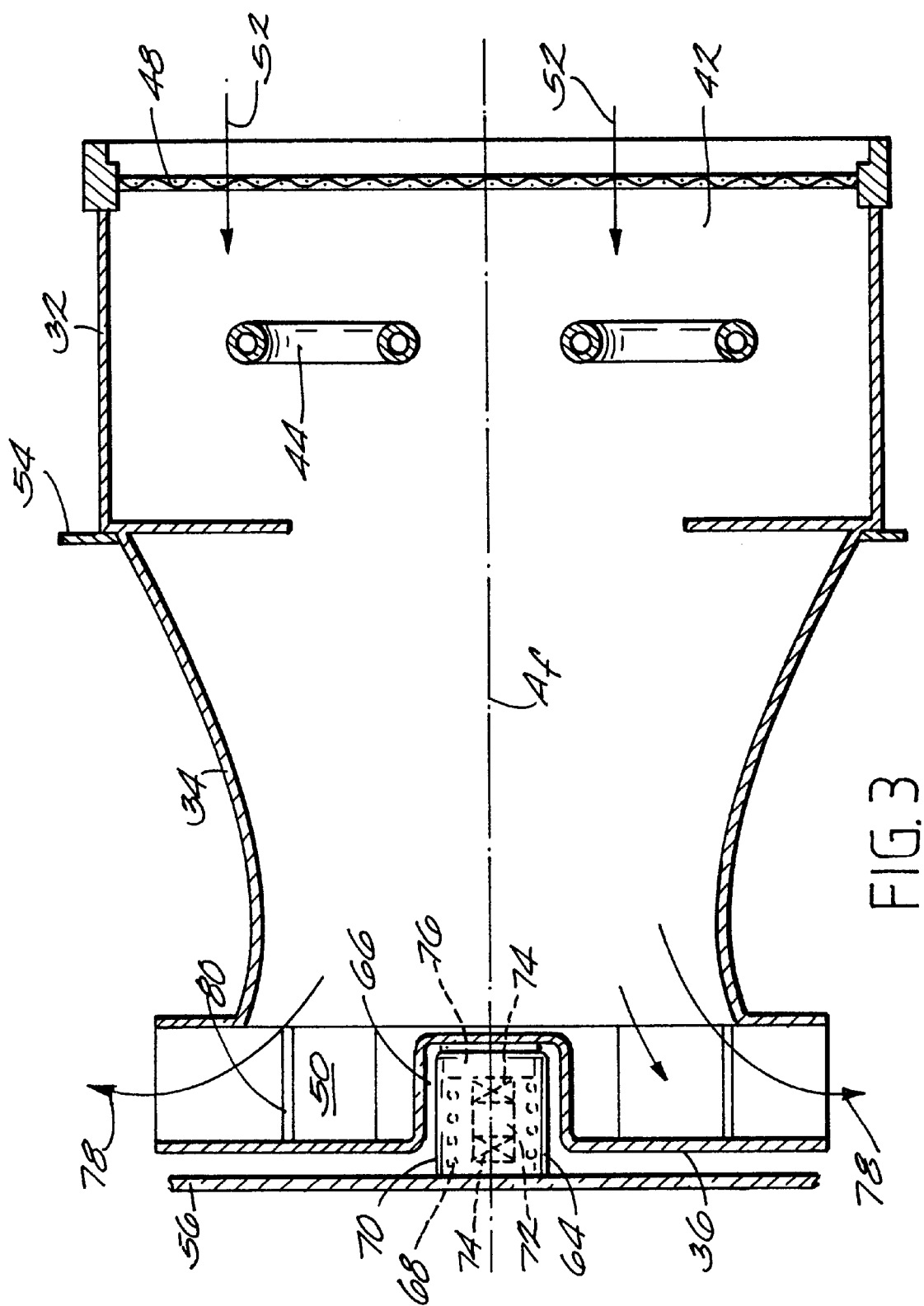
FIG. 3 is a sectional view taken along lines 3—3 of FIG. 2.

Referring to FIGS. 2 and 3 together, there is shown chamber 42 of heat exchanger 32 connected through the air shroud 34 to an interior chamber 50 of radial fan 36. Thus, when fan 36 is rotatably driven, air is drawn into and through chamber 42, in the direction shown by arrow 52. Such direction is generally parallel to the axis $A_f$. As the air moves past respective segments of tubing 44, heat is transferred to the air from the cooling oil 46. To maximize efficiency, shroud 34 forms a tight seal with fan 36 around the opening into chamber 50, and also with the heat exchanger 32 around the opening into chamber 42.

Referring further to FIGS. 2 and 3, there is shown heat exchanger 32, air shroud 34, and radial fan 36 respectively supported by a frame comprising substantially flat wall members 54 and 56. Wall members 54 and 56 are joined together in spaced apart parallel relationship by means of lateral member 58 and 60, which are selectively spaced apart from fan 36. Lateral members 58 and 60 are joined to wall members 54 and 56, by means of welding, screws, (not shown), or other suitable means. Bolt holes 62 are provided at an end of each of the wall members, for receiving bolts (not shown) to fasten the wall members and cooling arrangement 26 supported thereby to the gantry 12 or X-ray tube 14.

Referring further to FIG. 3, there is shown a motor 64 in simplified form, fixably joined to wall member 56 by suitable means. Motor 64 substantially resides in a well 66 formed in fan 36, and is provided with stator windings 68 within motor casing 70. Motor 64 is further provided with a rotor 72, which is journaled in casing 70 by means of bearings 74 and aligned along the axis $A_f$. The radial fan 36 is joined to rotor 72 by means of a linking member 76, so that the fan is rotatably driven by the rotor. Linking member 76 supports fan 36 so that the fan axis comprises axis $A_f$. Thus, respective components of motor 64 serve to cantilever radial fan 36 from wall member 56, and orient fan axis $A_f$ in parallel relationship with gantry axis $A_g$. When electric power is supplied to motor 64 through a set of leads (not shown), stator 68 is actuated to rotatably drive rotor 72 and fan 36.

Because the axis of radial fan 36 is in parallel relationship with gantry axis $A_g$, gyroscopic forces created by gantry rotation are not applied to the rotating fan. In the absence of such parallel relationship, gantry rotation would apply a non-zero torque to the fan, perpendicular to the fan axis, which could seriously reduce fan life. For example, testing of an embodiment of the invention demonstrated that the parallel relationship between the fan and gantry axes increased fan life on the order of twelve times, with respect to fan and gantry axes in orthogonal or other non-parallel relationship.

FIGS. 2 and 3 show radial fan 36 provided with blades or impellers 80. When impellers 80 are rotated, an intake air stream is moved along axis $A_f$ into the fan 36, as described above. The air is then exhausted radially, i.e., it is moved outwardly from fan 36, away from axis $A_f$ as indicated by arrows 78 in FIG. 3.

By using a radial fan rather than an axial fan of the prior art, the speed of fan rotation can be decreased without significantly reducing cooling power. For example, it has been found that if an embodiment of the invention is driven at a reduced speed of 1900 rpm, a first harmonic noise component of only 315 Hz is generated. Accordingly, the second harmonic component of the noise, on the order of 750 Hz, is likewise well below the 1000 Hz "annoyance factor" threshold. The embodiment did not generate any higher order components of significant amplitude. At the same time, cooling oil leaving the heat exchanger was only on the order of two degrees centigrade warmer than the temperature thereof when the fan was operated at a much higher speed.

Figure 4:
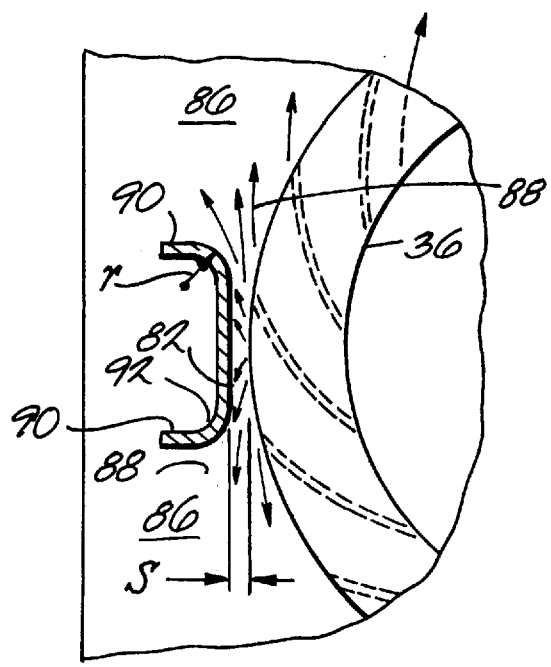
FIG. 4 is a sectional view taken along lines 4—4 of FIG. 2.

To further reduce noise, the frame used with radial fan 26 is provided with lateral members 58 and 60, rather than the struts used with prior art axial fans. Thus, blade pass-by noise caused by the struts is eliminated. In positioning lateral members 58 and 60, it is desirable to have them in closely spaced relationship with the edges of impellers 80, to provide sufficient structural support as well as to enhance compactness in the construction of cooling arrangement 26. A preferred spacing S is on the order of 1.0–1.5 centimeters. However, as best shown by FIG. 4, the radially exhausted air creates a region 82 of high pressure air between the fan 36 and each of the lateral members 58 and 60. Such high pressure air flows to regions 86 of lower pressure air, proximate to edges 90 of lateral members 58 and 60. To smooth such air flow, depicted in FIG. 4 by arrows 88, a bend 92 having a radius r is formed in the two opposing side edges 90 of each of the lateral members 58 and 60. Preferably, such bend radius r is on the order of 5.0 millimeters.

Figure 5:
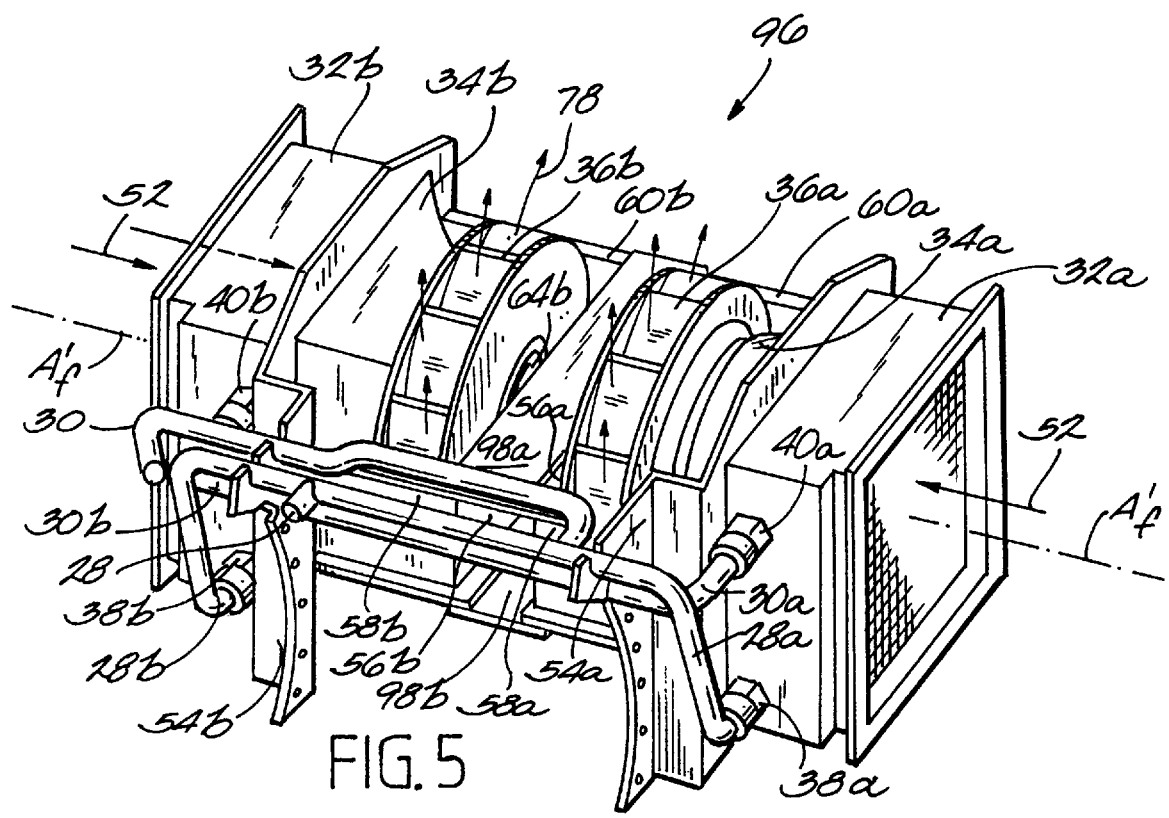
FIG. 5 is a perspective view showing a modification of the embodiment of FIG. 1.

Referring to FIG. 5, there is shown a second embodiment 96 of the invention. Such embodiment comprises two radial fans 36a and 36b, aligned in coaxial relationship along an axis $A_f'$. Embodiment 96 further comprises heat exchangers 32a and 32b, and air shrouds 34a and 34b, associated with fans 36a and 36b, respectively. Fans 36a and 36b, heat exchangers 32a and 32b, and air shrouds 34a and 34b are similar or identical to fan 36, heat exchanger 32 and air shroud 34 respectively, of cooling arrangement 26 described above. FIG. 5 further shows embodiment 96 provided with wall member 54a and 56a, respectively similar to wall members 54 and 56, which support the fan 26a, heat exchanger 32a, and air shroud 34a in operative relationship in like manner with cooling arrangement 26. Similarly. wall members 54b and 56b support the fan 26b, heat exchanger 32b, and shroud 34b in like manner with cooling arrangement 26. The wall members 56a and 56b are attached to one another by upper and lower members 98a and 98b, respectively, which join the two sections of embodiment 96 into a single structure.

Referring further to FIG. 5, there is shown the hose 28 feeding into two hose segments 28a and 28b, which are respectively coupled to inlet port 38a of heat exchanger 32a, and to inlet port 38b of heat exchanger 32b. In like manner, hose 30 is coupled to receive cooling oil from both hose segments 30a and 30b, respectively coupled to outlet port 40a of heat exchanger 32a and outlet port 40b of heat exchanger 32b. Thus, approximately half the oil coming from X-ray tube 14 is routed to each of the heat exchangers 32a and 32b, for cooling thereby. Accordingly, embodiment 96 of the invention provides twice the cooling capacity of cooling arrangement 26, shown in FIG. 2, and yet is still comparatively compact.

FIG. 5 shows fan 36b cantilevered from wall member 56b by a motor 64b, which is identical or similar to motor 64, the fan 36b being driven by motor 64b. Fan 36a is mounted upon and driven by a motor (not shown) which is likewise similar or identical to motor 64 and is attached to wall member 56a. Embodiment 96 is further provided with lateral members 58a and 58b which are respectively similar to lateral member 58, and with lateral members 60a and 60b which are respectively similar to lateral member 60.

Obviously, numerous other modifications and variations of the present invention are possible in light of the above teachings. It is therefore to be understood that within the scope of the disclosed concept, the invention may be practiced otherwise than as specifically described.

What is claimed is:

1. A cooling apparatus disposed for use with an X-ray tube mounted on the gantry of a CT system, the gantry being rotatable about a gantry axis, said apparatus comprising:
   a frame fixably joined for rotation with said gantry about said gantry axis;
   means for providing a path of flow for X-ray tube coolant fluid between said X-ray tube and a location proximate to said frame;
   a fan disposed to move a stream of air past a portion of said path of flow to remove heat from said coolant fluid as it flows through said portion, said fan comprising a radial fan; and
   means for rotatably mounting said radial fan on said frame so that the axis of rotation of said fan is in substantially parallel relationship with said gantry axis.

2. The apparatus of claim 1 wherein:
   said radial fan comprises an arrangement of impellers positioned around an interior chamber and is rotatable to draw a stream of air through a selected spatial volume enclosing said portion of said flow path, and to thereafter draw said stream of air into said chamber and then exhaust said stream of air radially with respect to said fan axis.

3. The apparatus of claim 2 wherein:
   said frame includes a selected number of flat structural members in spaced-apart relationship from the edges of said impellers, each of said members lying in the path of a portion of said radially exhausted air and having side edges which are selectively shaped to reduce turbulence as said portions of exhausted air flow from regions of comparatively high pressure to adjacent regions of lower pressure.

4. The apparatus of claim 3 wherein:
   the side edges of each of said flat structural members are respectively provided with bends of a specified bend radius.

5. The apparatus of claim 4 wherein said means for providing said flow path comprises:
   a heat exchange device having a length of conduit comprising said portion of said path of flow, said conduit having opposing first and second ends respectively communicating with an inlet port and an outlet port of said heat exchange device, said heat exchange device constructed to enable said stream of air to flow past said conduit to remove heat from said cooling fluid flowing therethrough;
   a first hose connected between said X-ray tube and said inlet port; and
   a second hose connected between said X-ray tube and said outlet port.

6. A cooling apparatus disposed for use with an X-ray tube mounted on the gantry of a CT system, the gantry being rotatable about a gantry axis, said apparatus comprising:
   a frame fixably joined for rotation with said gantry about said gantry axis;
   a heat exchanger mounted on said frame;
   means for providing a path of flow for circulating a coolant fluid between said X-ray tube and said heat exchanger, a specified portion of said path lying within said heat exchanger;

a radial fan disposed to move a stream of air through said heat exchanger to remove heat from said coolant fluid as it flows through said specified portion of said path, said fan comprising a radial fan; and means for driving said radial fan, and for rotatably mounting said radial fan on said frame so that the axis of rotation of said fan is in substantially parallel relationship with said gantry axis.

7. The apparatus of claim 6 wherein:

said fan comprises an arrangement of impellers positioned around an interior chamber, and is rotatable to draw said stream of air through said heat exchanger and into said chamber, and to then exhaust said stream of air radially with respect to said fan axis.

8. The apparatus of claim 7 wherein:

said frame includes a selected number of flat structural members in spaced-apart relationship from the edges of said fan impellers, each of said members lying in the path of a portion of said radially exhausted air and having side edges which are selectively shaped to reduce turbulence as said portions of exhausted air flow from regions of comparatively high pressure to adjacent regions of lower pressure.

9. The apparatus of claim 8 wherein:

the side edges of said flat structural members are respectively provided with bends of a specified bend radius.

10. The apparatus of claim 9 wherein:

said flat structural members are spaced apart from said fan impellers on the order of 1.0–1.5 centimeters, and said specified bend radius is on the order of five millimeters.

11. The apparatus of claim 6 wherein:

said heat exchanger and said radial fan comprise a first heat exchanger and a first radial fan respectively; and said apparatus further comprises means for driving said second radial fan, and for rotatably mounting said second radial fan on said frame so that said second radial fan is in coaxial relationship with said first radial fan.

12. The apparatus of claim 11 wherein:

said means for providing said path of flow comprises means for moving approximately half of the coolant fluid flowing from said X-ray tube through each of said heat exchangers; and said second radial fan is disposed to move a stream of air through said second heat exchanger to remove heat from said coolant fluid moving therethrough.

* * * * *